US012685484B2

(12) United States Patent
Hasbeck et al.

(10) Patent No.: US 12,685,484 B2
(45) Date of Patent: Jul. 21, 2026

(54) OSTOMY SYSTEM WITH ACCESSORY DEVICE, AND RELATED METHODS FOR MONITORING AN OSTOMY SYSTEM

(71) Applicant: Coloplast A/S, Humlebaek (DK)

(72) Inventors: Lilith Louise Lysgaard Hasbeck, Copenhagen NV (DK); Jonas Emborg, Frederikssund (DK); Jesper Kenneth Olsen, Birkeroed (DK); Jais Ask Hansen, Jaegerspris (DK)

(73) Assignee: Coloplast A/S, Humlebaek (DK)

( * ) Notice: Subject to any disclaimer, the term of this patent is extended or adjusted under 35 U.S.C. 154(b) by 895 days.

(21) Appl. No.: 17/918,616

(22) PCT Filed: Apr. 14, 2021

(86) PCT No.: PCT/DK2021/050103
§ 371 (c)(1),
(2) Date: Oct. 13, 2022

(87) PCT Pub. No.: WO2021/209103
PCT Pub. Date: Oct. 21, 2021

(65) Prior Publication Data
US 2023/0147665 A1 May 11, 2023

(30) Foreign Application Priority Data
Apr. 14, 2020 (DK) ........................... PA 2020 70228

(51) Int. Cl.
*A61F 5/448* (2006.01)
*A61B 5/00* (2006.01)
(Continued)

(52) U.S. Cl.
CPC ............ *A61B 5/4851* (2013.01); *A61F 5/448* (2013.01); *A61F 5/443* (2013.01); *A61F 5/445* (2013.01)

(58) Field of Classification Search
CPC ........ A61B 5/4851; A61F 5/448; A61F 5/443; A61F 5/445
See application file for complete search history.

(56) References Cited

U.S. PATENT DOCUMENTS 10,500,084 B2 * 12/2019 Hansen ................. A61F 5/4404
11,491,042 B2 * 11/2022 Seres .................... G01F 23/261
(Continued)

FOREIGN PATENT DOCUMENTS

CN       102470041 B     10/2014
CN       110840438 A      2/2020
(Continued)

*Primary Examiner* — Guy K Townsend
(74) *Attorney, Agent, or Firm* — Coloplast Corp., Coloplast A/S; Nick Baumann

(57) ABSTRACT

The present disclosure provides an accessory device of an ostomy system and related methods including a method, performed in an accessory device, for monitoring an ostomy system comprising a monitor device and an ostomy appliance comprising a base plate configured to be placed on a skin surface of a user, wherein the accessory device comprises an interface configured to communicate with at least the monitor device of the ostomy system, the method comprising obtaining monitor data from the monitor device, the monitor data being indicative of a condition of the ostomy system; determining, based on the monitor data, an operating state of the ostomy system in a first time period after a first event; in accordance with the operating state of the first time period being a first primary operating state, communicating a first primary indication via the interface; determining, based on the monitor data, an operating state of the ostomy system in a second time period after the first time period; and in accordance with the operating state of the second time period being the first primary operating state, communicating a second indication different from the first primary indication via the interface.

9 Claims, 14 Drawing Sheets

(51) Int. Cl.
    *A61F 5/443*         (2006.01)
    *A61F 5/445*         (2006.01)

(56)               References Cited

U.S. PATENT DOCUMENTS

| | | | |
|---|---|---|---|
| 11,534,323 B2 * | 12/2022 | Hansen | G16H 30/40 |
| 12,029,582 B2 * | 7/2024 | Svanegaard | A61B 5/4851 |
| 12,127,966 B2 * | 10/2024 | Hansen | A61F 5/445 |
| 12,369,853 B2 * | 7/2025 | Nielsen | A61F 5/443 |
| 2017/0140103 A1 * | 5/2017 | Angelides | A61F 5/4404 |
| 2019/0192332 A1 * | 6/2019 | Hansen | A61B 5/7475 |
| 2019/0192334 A1 | 6/2019 | Hansen et al. | |
| 2020/0375785 A1 * | 12/2020 | Hansen | A61B 90/361 |
| 2020/0405229 A1 * | 12/2020 | Svanegaard | A61F 5/443 |
| 2020/0405230 A1 * | 12/2020 | Svanegaard | A61B 5/6813 |
| 2021/0059603 A1 * | 3/2021 | Svanegaard | A61B 5/4851 |
| 2021/0361467 A1 * | 11/2021 | Hansen | A61F 5/4404 |
| 2021/0369197 A1 * | 12/2021 | Hansen | A61B 5/4851 |
| 2021/0369489 A1 * | 12/2021 | Hansen | A61F 5/4404 |
| 2023/0059470 A1 * | 2/2023 | Hansen | A61F 5/443 |
| 2023/0147665 A1 * | 5/2023 | Hasbeck | A61F 5/445 |
| | | | 604/339 |
| 2024/0306991 A1 * | 9/2024 | Svanegaard | A61B 5/4851 |
| 2025/0064394 A1 * | 2/2025 | Hansen | A61B 5/4851 |

FOREIGN PATENT DOCUMENTS

| | | | | |
|---|---|---|---|---|
| CN | 109561980 B | 9/2021 | | |
| WO | 2019120432 A1 | 6/2019 | | |
| WO | 2019161860 A1 | 8/2019 | | |
| WO | WO-2019161863 A1 * | 8/2019 | ........ | H04M 1/72409 |
| WO | 2020003351 A1 | 1/2020 | | |

* cited by examiner

4

211

210

290, 290A 292, 292A 288, 288A 286, 286A 282, 282A 284, 284A 8, 400

OSTOMY SYSTEM WITH ACCESSORY DEVICE, AND RELATED METHODS FOR MONITORING AN OSTOMY SYSTEM

The present disclosure relates to an accessory device of an ostomy system and related methods for monitoring an ostomy system. The ostomy system comprises an ostomy appliance, an accessory device and a monitor device. In particular, the present disclosure relates to methods for monitoring an ostomy system and parts thereof.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
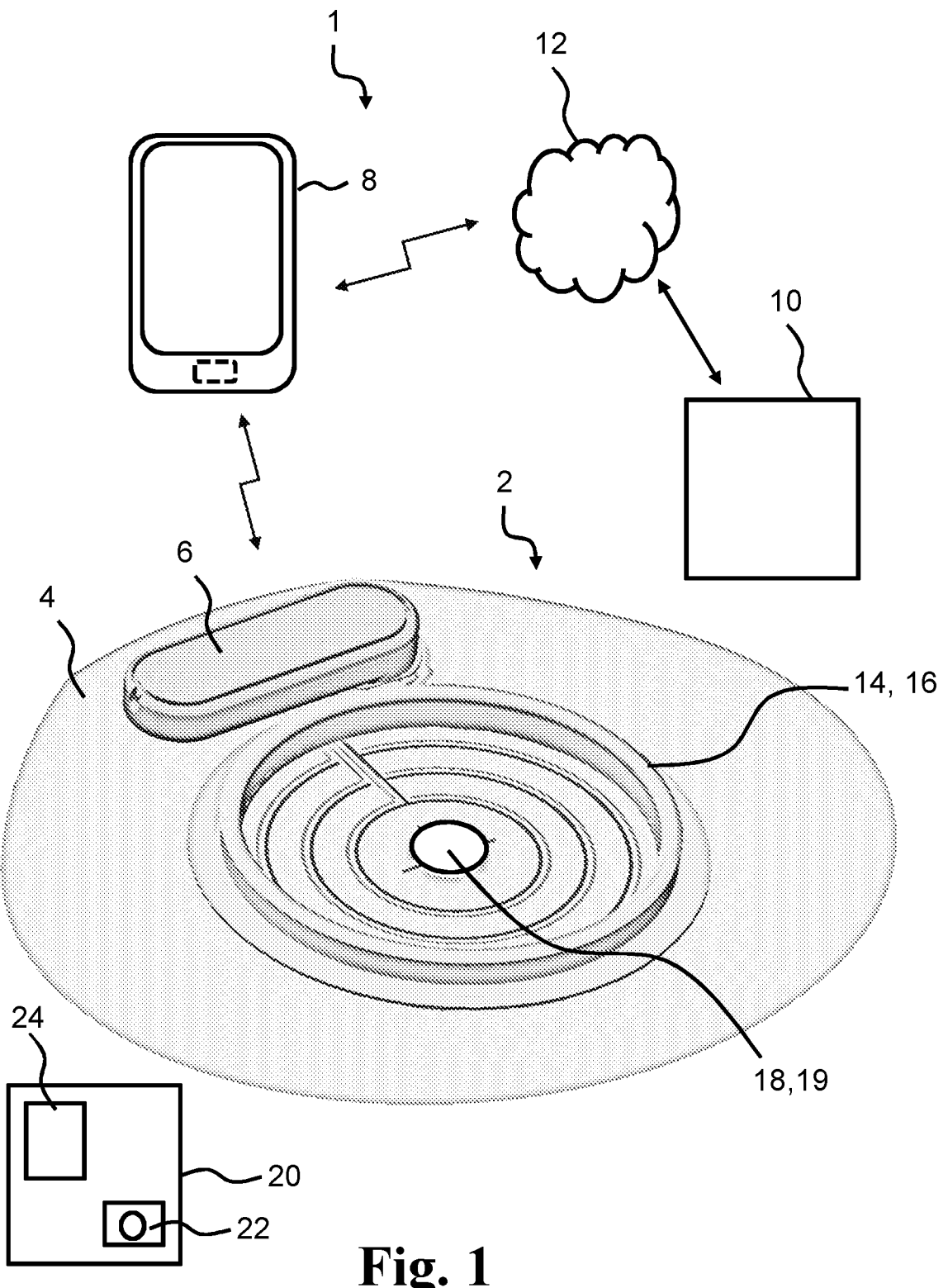
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices, and related methods. Further, methods related to an accessory device of the ostomy system and accessory devices thereof are disclosed. An accessory device (also referred to as an external device) may be a mobile phone or other handheld device. An accessory device may be a personal electronic device, e.g. a wearable, such as a watch or other wrist-worn electronic device. The ostomy system may comprise a docking station. An accessory device may be a docking station. An accessory device may act as a docking station. The docking station may be configured to electrically and/or mechanically couple the monitor device to the docking station. The docking station may be configured for charging the monitor device and/or configured for transferring data between the monitor device and the docking station, and/or between the accessory device and the docking station and/or between the monitor device and the accessory device via the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation or moisture presence in and/or at the adhesive material provided for attaching the base plate to the skin surface of a user. Depending on the nature of the pattern of moisture propagation and/or presence in and/or at the adhesive material, the ostomy system and devices thereof enable providing information to the user about the type of failure, and in turn enable providing an indication to the user of an internal state of the ostomy system or severity and thus the remaining time frame for replacing the ostomy appliance/base plate without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area. The ostomy appliance may comprise an electrode assembly or the ostomy system optionally comprises an electrode assembly mountable on a proximal side of the base plate of the ostomy appliance. The electrode assembly, also denoted sensor assembly, comprises a plurality of electrodes optionally arranged on a distal side of a first adhesive layer of the ostomy appliance or on a distal side of a first adhesive layer of the electrode assembly, the plurality of electrodes forming a plurality of sensors (electrode pairs). The ostomy appliance/electrode assembly may comprise a monitor interface for connecting electrodes of the electrode assembly to terminals of the first interface of the monitor device.

The base plate and/or electrode assembly comprises a first adhesive layer, also denoted centre adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer may have a stomal opening with a centre point. A base plate with at least three electrodes having sensing parts with contact to the first adhesive layer allows for determining erosion/ swelling properties or characteristics of the first adhesive layer and/or determining a degree of erosion and/or swelling of the first adhesive layer.

It is appreciated that the sensing/monitoring functionalities of a base plate as described herein may as well be provided by means of a separate sensor patch configured for attachment to a proximal surface of a conventional base plate. For example, the sensor patch may be a layer comprising an adhesive layer, such as a first adhesive layer, an electrode assembly, and a monitor interface for coupling to a monitor device. Thereby, the sensor patch may be adhered, such as by a user preparing the base plate, to the proximal (adhesive) surface of a conventional base plate, such that said base plate can achieve the functionalities as described herein.

It is an advantage of the present disclosure that an optimum or improved use of an ostomy appliance is provided. In particular, the present disclosure facilitates that a base plate is not changed too early (leading to increased cell-stripping from the skin and increased risk of skin damage and further leading to increased costs and/or material waste) nor too late (leading to adhesive failure, leakage and/or skin damage from the aggressive output). Accordingly, the user or a health care professional is able to monitor and plan the use of the ostomy appliance. Further, the present disclosure allows improved monitoring of an ostomy system by being able to notify a user more precisely on an internal state of the ostomy system/ostomy appliance/base plate, e.g. about reasons behind moisture presence and/or propagation.

Further, determination of operating states and classification of operating states of the ostomy appliance in different time periods is useful in helping to reduce the risk of a user experiencing leakage from an ostomy appliance and in general providing improved feedback to the user about handling and operation of the ostomy system. Further, determination of operating states and classification of operating states of the ostomy appliance is further useful in helping reduce the risk of skin damage to a user. In particular, determination of operating states according to the present disclosure may help provide a clear distinction or differentiation between mishandling of the ostomy appliance, e.g. during application of the ostomy appliance, adhesive failure, leakage of output, which is harmful to the skin, and a sweating ostomate.

In particular, embodiments of the present disclosure provide for communicating different indications based on the same operating state, but the different indications being communicated in different time periods. Thereby, the same operating state may be interpreted/communicated, e.g. by the accessory device, differently depending on the time period in which it occurred. For example, an operating state indicative of the presence of liquid in the interface between the skin surface and a proximal surface of the base plate may be caused by different mechanisms dependent on the time in which the operating state was determined: if such operating state (the presence of liquid) is determined immediately after application of the base plate to the skin surface (e.g., in a first time period), the liquid is more likely water (e.g. due to insufficient cleaning/preparation of the skin) than output emanating from the stoma, whereas if such operating state (the presence of liquid) is determined later on (e.g., in a second time period), the liquid is more likely output propagating in the interface than water.

The present disclosure provides a simple, efficient, and easy-to-use ostomy system with a high degree of comfort for a user by improving feedback to the user on internal state of the base plate.

A method, performed in an accessory device, for monitoring an ostomy system comprising a monitor device and an ostomy appliance comprising a base plate configured to be placed on a skin surface of a user is disclosed. The accessory device comprises an interface configured to communicate with at least the monitor device of the ostomy system, the method comprising obtaining monitor data from the monitor device, the monitor data being indicative of a condition of the ostomy system; determining, based on the monitor data, an operating state of the ostomy system, e.g. an operating state of the base plate, in a first time period e.g. after a first event; in accordance with the operating state of the first time period being a first primary operating state, communicating a first primary indication via the interface; determining, based on the monitor data, an operating state of the ostomy system in a second time period, e.g. after the first time period and/or after a second event; and in accordance with the operating state of the second time period being the first primary operating state, communicating a second primary indication different from the first primary indication via the interface.

The method optionally comprises determining whether the operating state of the first time period is a first primary operating state.

The method optionally comprises determining whether the operating state of the second time period is a first primary operating state.

The operating state of the ostomy system may comprise an operating state of the base plate, the operating state of the base plate optionally being indicative of an adhesive performance of the base plate and/or indicative of presence of fluid, such as one or more of output, water, sweat, and mucus, on the proximal side or surface of the first adhesive layer.

The operating state of the ostomy system may comprise an operating state of the ostomy appliance and/or an operating state of a connection between the ostomy appliance and the monitor device.

The first event may be a connection event of the monitor device being connected to the ostomy appliance. A connection event of the monitor device being connected to the ostomy appliance may be detected by the monitor device and a connection indicator, such as a connection time stamp, may be included in the monitor data. The first event may be an application event of the ostomy appliance being applied on the skin of the user. The first event may be a connection event of the monitor device being connected to the accessory device. A connection event of the monitor device being connected to the accessory device may be detected by the accessory device. The first event may be a user input event of a user input indicative of the first event, e.g. where the accessory device detects a user input, e.g. on a user interface object on touch sensitive display. The first event may be a user input event of a user input indicative of the first event, e.g. where the monitor device detects a user input.

In one or more exemplary methods, an end of the first period may trigger or be the beginning of the second period. In other words, the first period and the second period may be separate and non-overlapping.

In one or more exemplary methods, a second event may trigger or be the beginning of the second period. The second event may be a user input event of a user input indicative of the second event, i.e. where the accessory device detects a user input, e.g. on a user interface object on touch sensitive display. The second event may be a time after a user input event of a user input indicative of the second event, such as 30 seconds after the user has indicated that the ostomy system is ready for use, i.e. that the application/mounting routine is done.

The monitor data may be indicative of a physical condition of a base plate, e.g. indicative of a dynamic internal state of the base plate. The monitor data may be indicative of a moisture content in the base plate/first adhesive layer and/or at the first adhesive layer, such as between the first adhesive layer and the skin of a user.

In one or more exemplary methods for monitoring an ostomy system, the method comprises receiving, via the interface, a user input indicative of the first event, e.g. via touch-sensitive display, such as by a user tapping a user interface object of a user interface.

In one or more exemplary methods for monitoring an ostomy system, the ostomy appliance comprises a base plate, the base plate comprising a first adhesive layer having a proximal side, and one or more electrodes configured to measure electrical properties at or in the first adhesive layer, wherein obtaining the monitor data comprises obtaining ostomy data representative of the electrical properties.

In one or more exemplary methods for monitoring an ostomy system, the first time period has a first period length less than 15 minutes. The first period length may be less than 10 minutes, such as in the range from 1 second to 5 minutes, such as 2 minutes, 3 minutes or 4 minutes. In one or more exemplary methods, the first time period has a first period length less than 1 minute, such as in the range from 15 seconds to 45 seconds. A relatively short first time period, such as less than 1 minute, may be sufficient to detect possible mishandling while not delaying the user in the application routine.

In one or more exemplary methods for monitoring an ostomy system, the first primary operating state is indicative of presence of liquid or fluid, such as water, output, sweat, and/or mucus, on a proximal side of the base plate.

The primary operating state may represent or be indicative of presence of fluid on the proximal side of the first adhesive layer of the base plate/electrode assembly.

In one or more exemplary methods for monitoring an ostomy system, communicating the first primary indication comprises displaying, on a display of the accessory device, a first primary user interface object. The first primary user interface object may be indicative of a mishandling of the ostomy appliance, e.g. during application of the base plate, such as indicative of a wet mount of the ostomy appliance. A wet mount is understood as liquid, such as water, sweat, mucus, and/or output, being present between the first adhesive layer of the base plate/electrode assembly and the skin of the user during and/or shortly after application of the baseplate.

The method may comprise determining a first primary indication e.g. based on a first time after the first event or start of the first time period. The first primary user object may indicate one or more of the first time, the first primary operating state, a reason for the first primary operating state, and a recommended action. The first primary user object may comprise first primary text. Examples of first primary text may be "Liquid has been detected between the base plate and your skin. This may be due to a misapplication of your baseplate", "Your skin is wet. Please change your base plate and make sure to dry or clean your skin properly". "Liquid was detected 10 seconds after application due to a wet mount of your base plate. Please change".

The first primary user object may be split into a plurality of first primary user interface objects.

Determining a first primary indication may comprise selecting a first primary user interface object from a set of user interface objects.

In one or more exemplary methods for monitoring an ostomy system, communicating the second primary indication comprises displaying, on a display of the accessory device, a second primary user interface object. The second primary user interface object may be indicative of a possible leakage of output.

The method may comprise determining a second primary indication e.g. based on a second time after the second event or start of the second time period. The second primary user object may indicate one or more of the second time, the first primary operating state, a reason for the first primary operating state, and a recommended action. The second primary user object may comprise second primary text. Examples of second primary text may be "Liquid has been detected between the base plate and your skin. There is a high risk of leakage" and "Check your base plate. A leakage could be imminent".

The second primary user interface object may be split into a plurality of second primary user interface objects.

Determining a second primary indication may comprise selecting a second primary user interface object from a set of user interface objects.

In one or more exemplary methods for monitoring an ostomy system, the method comprises, in accordance with the operating state in the first time period being a first secondary operating state, communicating a first secondary indication via the interface. The first secondary operating state may be indicative of a mishandling of the monitor device during coupling of the ostomy appliance/electrode assembly and/or be indicative of faulty connection between the ostomy appliance and the monitor device. Communicating a first secondary indication via the interface may comprise displaying a first secondary user interface object and/or outputting a first secondary audio output.

The method optionally comprises determining whether the operating state of the first time period is a first secondary operating state.

In one or more exemplary methods for monitoring an ostomy system, communicating the first secondary indication comprises displaying, on a display of the accessory device, a first secondary user interface object. The first secondary user interface object may be indicative of a faulty connection between the monitor device and the ostomy appliance, e.g. due to presence of liquid in the connection between the monitor device and the ostomy appliance, such as comprising a first secondary text, e.g. "The connection between monitor device and ostomy appliance is wet. Please keep the connection dry".

The method optionally comprises determining whether the operating state of the second time period is a first secondary operating state.

In one or more exemplary methods for monitoring an ostomy system, the method comprises, in accordance with the operating state in the second time period being a first secondary operating state, communicating a second secondary indication via the interface. The second secondary indication may be different from the first secondary indication. Communicating a second secondary indication via the interface may comprise displaying a second secondary user interface object different from the first secondary user interface object. The second secondary user interface object may be indicative of water ingress in the connection between the monitor device and the ostomy appliance in the second time period. The second secondary user interface object may comprise a second secondary text, e.g. "Water ingress has occurred in the connection after application. Please clean and dry the connection".

Also, an accessory device for an ostomy system comprising an ostomy appliance, a monitor device, and the accessory device is disclosed, the accessory device comprising: a processor; a memory connected to the processor; and an interface configured to connect the accessory device to the monitor device, the interface comprising a transceiver module connected to the processor, wherein the accessory device is configured to: obtain monitor data, e.g. from the monitor device connected or connectable to the accessory device, the monitor data being indicative of a condition of the ostomy system, such as one or more of the ostomy appliance, the monitor device, and the connection between the ostomy appliance and the monitor device; determine, based on the monitor data, an operating state of the ostomy system in a first time period, e.g. after a first event; in accordance with the operating state of the first time period being a first primary operating state, communicate a first primary indication via the interface; determine, based on the monitor data, an operating state of the ostomy system in a second time period, e.g. after the first time period or after a second event; and in accordance with the operating state of the second time period being the first primary operating state, communicate a second indication different from the first primary indication via the interface.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output, such as user interface objects displayed on the display, optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second user interface object or a plurality of second user interface objects, such as second primary user interface object and/or a second secondary user interface object. A user interface object, such as the first primary user interface object and/or the second user interface object, may represent an operating state of the base plate in a time period.

In one or more exemplary accessory devices, the accessory device is configured to receive, via the interface, a user input indicative of the first event.

In one or more exemplary accessory devices, the ostomy appliance comprises an ostomy pouch and a base plate, the base plate comprising a first adhesive layer having a proximal side, and one or more electrodes configured to measure electrical properties at or in the first adhesive layer, and wherein to obtain the monitor data comprises to obtain ostomy data representative of the electrical properties.

In one or more exemplary accessory devices, the first time period has a first period length less than 15 minutes.

In one or more exemplary accessory devices, the first primary operating state is indicative of presence of liquid on a proximal side of the base plate.

In one or more exemplary accessory devices, the interface comprises a display, and wherein to communicate the first primary indication comprises to display, on the display, a first primary user interface object. The first primary user interface object may be indicative of a wet mount of the ostomy appliance.

A user interface refers herein to a graphical representation comprising a collection of user interface objects. A user interface comprises one or more user interface objects. A user interface may be referred to as a user interface screen or a graphical user interface.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini application that may be used by the user and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

In one or more exemplary accessory devices, to communicate the second primary indication comprises to display, on a display of the accessory device, a second user interface object indicative of a possible leakage of output.

In one or more exemplary accessory devices, the accessory device is configured to in accordance with the operating state in the first time period being a first secondary operating state, communicate a first secondary indication via the interface.

The first secondary operating state may be indicative of faulty connection between the ostomy appliance and the monitor device, such as in case of water ingress and/or output or other fluid being left in the connection at coupling. In other words, the accessory may be configured to determine that the connection between the monitor device and the ostomy appliance/sensor assembly is faulty and in accordance with a determination that the connection is faulty, communicate a first secondary indication via the interface. The first secondary indication may represent the first secondary operating state.

In one or more exemplary accessory devices, to communicate the first secondary indication comprises to display, on the display, a first secondary user interface object indicative of a faulty connection between the monitor device and the ostomy appliance.

Is to be noted that descriptions of the accessory device being configured to perform acts also apply to the corresponding acts in the method of operating an accessory device and vice versa.

Further, a computer readable storage medium storing one or more programs is disclosed, the one or more programs comprising instructions, which when executed by an accessory device with an interface, a memory and a processor cause the accessory device to operate in accordance with the method for monitoring an ostomy system as described herein.

An ostomy system comprising an ostomy appliance, a monitor device, and an accessory device is disclosed, wherein the accessory device is an accessory device as described herein.

An ostomy appliance comprises a first adhesive layer. The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the centre point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the centre point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer, also denoted rim adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a centre point.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate, such as an electrode assembly of the base plate, or an electrode assembly configured for mounting on the proximal surface of the base plate comprises one or more electrodes, such as a plurality of electrodes, such as two, three, four, five, six, seven or more electrodes. The electrodes, e.g. some or all the electrodes and/or parts thereof, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The electrode assembly may be embodied as an add-on to the base plate and be configured for mounting on the proximal surface of the base plate. Thus, the electrode assembly may be said to comprise the first adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode and/or a seventh electrode. The base plate, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly may have a stomal opening with a centre point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a centre point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a centre point. The top layer may have a thickness in the range from 0.01 mm to 1.0 mm, e.g. in the range from 0.02 mm to 0.2 mm, such as 0.04 mm.

The base plate comprises a monitor interface. The monitor interface may be configured for connecting, such as electrically and/or mechanically connecting, the ostomy appliance (base plate) to the monitor device. In other words, the ostomy appliance may be connected, connectable, or configured to connect to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven, eight or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

The base plate may comprise a coupling ring or other coupling member for coupling an ostomy pouch to the base plate (two-part ostomy appliance). The centre point may be defined as a centre of the coupling ring.

The base plate has a stomal opening with a centre point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor and one or more interfaces, such as a first interface and/or a second interface. The first interface is configured for connecting the monitor device to the ostomy appliance/baseplate. The second interface is configured for wirelessly connecting the monitor device to the accessory device. The monitor device may comprise a memory for storing ostomy data or appliance data.

The monitor device/processor is configured to obtain appliance data, such as ostomy data or parameter data based on ostomy data, based on appliance measurements via the terminals of the first interface. The processor is configured to determine monitor data based on the appliance data. The monitor device/processor is configured transmit the monitor data to the accessory device.

The monitor data may comprise appliance data optionally indicative of a physical condition of the ostomy appliance, such as data indicative of resistance, voltage, current between one or more electrode pairs of the ostomy appliance/electrode assembly. The appliance data may comprise ostomy data indicative of a physical condition of the ostomy appliance and/or parameter data based on the ostomy data. In other words, the monitor device may comprise ostomy data and/or parameter data based on the ostomy data.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The monitor device may be connected, connectable, or configured to connect to the ostomy appliance/electrode assembly. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven, eight or more terminals, for forming electrical connections with respective terminals and/or electrodes of the ostomy appliance and/or for detecting a faulty connection between the monitor device and the ostomy appliance/base plate/electrode assembly. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal and/or a seventh terminal. In one or more exemplary monitor devices, the first interface has M terminals, wherein M is an integer in the range from 4 to 8.

The first interface of the monitor device may comprise a coupling part for forming a mechanical connection, such as a releasable coupling or connection between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor. Sensor data of one or more sensors of the monitor device may be included in the monitor device. Thus, the monitor data may comprise sensor data of one or more sensors of the monitor device.

The monitor device comprises a second interface connected to the processor. The second interface may be configured as an accessory interface for connecting, e.g. wirelessly connecting, the monitor device to the accessory device. The monitor device may be connected, connectable or configured to connect to a plurality of accessory devices. The second interface may comprise an antenna and a wireless transceiver, e.g. configured for wireless communication at frequencies in the range from 2.4 to 2.5 GHZ. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate of the ostomy appliance.

The ostomy system may comprise a docking station forming an accessory device of the ostomy system and/or in addition to the accessory device. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The present disclosure provides a method, performed in an accessory device, for monitoring of the ostomy system or parts thereof, such as one or more of the ostomy appliance, the monitor device and the connection between the ostomy appliance and the monitor device, at the accessory device. The accessory device comprises an interface configured to communicate with at least the monitor device and optionally the ostomy appliance/electrode assembly configured to be placed on a skin surface of a user or on any additional seals. The method comprises obtaining (e.g. receiving and/or retrieving) monitor data, e.g. from the monitor device. The monitor data is indicative of presence of fluid at a proximal side of the first adhesive layer of the ostomy appliance/electrode assembly, towards the skin surface. In one or more exemplary methods, the method comprises determining an operating state being a leakage state at the proximal side of the first adhesive layer of the ostomy appliance based on the monitor data, and communicating an indication indicative of the leakage state of the ostomy appliance via the interface. In other words, the monitor data can be seen as indicative of a moisture condition at a proximal side (or proximal surface) of the first adhesive layer of the ostomy appliance/electrode assembly. The presence of fluid at the proximal side (or proximal surface) of the first adhesive layer of the ostomy appliance may be derived at the accessory device based on monitor data.

In one or more exemplary methods, the method may comprise determining the operating state to be a first primary operating state based on the monitor data. The first primary operating state may be indicative of presence of liquid, such as output, mucus, sweat, and/or water, at the proximal side or surface of the first adhesive layer of the ostomy appliance/electrode assembly. A first primary operating state in the present disclosure may be indicative of the dynamic internal state of the ostomy appliance, related to the presence of fluid and/or liquid, such as output, mucus, sweat, and/or water, such as severity, imminence, timing of leakage at a proximal side (or proximal surface) of the ostomy appliance. By quickly identifying the presence of fluid/liquid, and determining an operating state as disclosed herein, the likelihood of ending in a situation where output has reached beyond the proximal side (or proximal surface), e.g. out to the clothes of the user, is significantly reduced. Such situation is extremely difficult for the user of the ostomy appliance, due to hygiene and social acceptance.

Presence of fluid, such as output, mucus, sweat, and/or water, on the proximal side (or proximal surface) of the first adhesive layer may affect, such as reduce, the adhesive performance of the ostomy appliance. Presence of output on the proximal side of the first adhesive layer affects a wear property, e.g. wear time and/or wear comfort of the ostomy appliance.

A first primary operating state in the present disclosure may be a leakage state and may indicate whether the ostomy appliance needs to be changed immediately based on presence of fluid at a proximal side (or proximal surface) of a first adhesive layer of the ostomy appliance and/or a possible reason for the presence of fluid. For example, the first primary operating state may be indicative of high risk of fluid going beyond the proximal side (or proximal surface) depending on a corresponding moisture pattern type.

The method comprises communicating (e.g. outputting, transmitting, displaying) a first primary indication via the interface. The first primary indication may be associated with the first primary operating state in the first period.

It is an advantage of the present disclosure that a user of an ostomy appliance or a health care professional is able to be advised on the status of the ostomy appliance and plan the change of the ostomy appliance. Further, the disclosed method allows for a more customized feedback on the dynamic internal state of the ostomy system, such as ostomy appliance, monitor device, and/or connection between the ostomy appliance and the monitor device. Communication of indications associated with the operating state of the ostomy appliance is useful in helping to reduce the risk of a user experiencing leakage from an ostomy appliance (e.g. faecal material leakage from the ostomy appliance), which stays long on the skin and increases risks of skin damage to a user (due to e.g. malfunctions and misplacement of the ostomy appliance on the stoma). Further, communication of indications associated with the operating state of the ostomy appliance is useful in helping the user in handling, such as applying, the ostomy appliance. In particular, determination of operating state and communication of indications according to the present disclosure is performed based on monitor data indicative of a presence of fluid at the proximal side (or proximal surface) of the ostomy appliance which is not be visible to the user (because it is under the base plate of the ostomy appliance) when the ostomy appliance is worn. This results in providing a clear improvement of the comfort provided by the ostomy appliance in that possible reasons for the presence of fluid is immediately communicated to the user via the accessory device and thereby allowing for a change to happen as soon as possible and/or allowing for a user to change the application routine for the ostomy appliance.

It is an important advantage that the ostomy system is able to advise an improved compliance towards optimal mounting/application routines including application of the ostomy appliance and coupling the monitor device to the ostomy appliance.

The present disclosure provides an efficient, and easy-to-use communication of an internal state of an ostomy appliance system with a high degree of comfort for a user. The present disclosure allows to derive and instantly (e.g. substantially in real time) communicate the indication based on monitor data that is not accessible or visible by the user or the health care professional. In other words, the disclosed method allows to indicate the dynamic internal state of the ostomy appliance to a user and/or reasons for the detected operating state, which allows a user to adapt routines results in preventing situations where leakage reached out to the clothes of the user and noticeable for others in the vicinity and eventually improving the life of the ostomate.

In one or more exemplary methods, the ostomy appliance comprises an ostomy pouch and a base plate. In one or more exemplary methods, the base plate comprises a first adhesive layer having a proximal side (or proximal surface). During use, a proximal surface at the proximal side of the first adhesive layer adheres to the user's skin in the peristomal area and/or to additional seals, such as sealing paste, sealing tape and/or sealing ring. In one or more exemplary methods, obtaining the monitor data comprises obtaining the monitor data indicative of the presence of fluid at the proximal side of a first adhesive layer of the base plate. The presence of fluid creates a conductive path at the proximal side of the first adhesive layer, such as on the proximal surface of the first adhesive layer, thus decreasing a resistance between electrodes of one or more electrode pairs arranged at or in the first adhesive layer.

In one or more exemplary methods, the monitor data comprises ostomy data and/or parameter data. For example, the parameter data is derived based on ostomy data. Ostomy data or parameter data based on the ostomy data are obtained from electrodes/sensors of the ostomy appliance with a monitor device. The monitor device may be configured to process the ostomy data and/or parameter data based on the ostomy data to determine monitor data that are transmitted to and received by the accessory device.

In one or more exemplary methods, a plurality of electrodes of base plate/electrode assembly are configured to detect presence of fluid on the proximal side in a primary sensing zone (and/or first zone) and a secondary sensing zone (and/or second zone) by measuring electrical properties between an electrode pair of the plurality of electrodes. The electrical properties may be indicative of a conductive path in or at the first adhesive layer, and thereby indicative of the presence of fluid at the proximal side of the first adhesive layer of the ostomy appliance. In one or more exemplary methods, obtaining monitor data comprises obtaining data representative of the measurements of the electrical properties at the proximal side of and/or in the first adhesive layer. In one or more exemplary methods, the ostomy data and/or parameter data are indicative of resistance between any two of the plurality of electrodes, capacitance and/or inductance between any two of the plurality of electrodes and/or any change thereof. In one or more exemplary methods, the ostomy data and/or parameter data are indicative of a change in resistance, capacitance and/or inductance between electrodes. In one or more exemplary methods, the ostomy data and/or parameter data comprises timing information, such as timestamped data or information from which timing is derivable.

In one or more exemplary methods, the monitor data comprises localized monitor data with respect to a location and/or a zone at the proximal side of the first adhesive layer of the base plate. Determining the operating state may comprise determining a leakage location and/or a leakage time information. The location and/or region at the proximal side of the first adhesive layer of the base place may be related to a position at the proximal side of the first adhesive layer where electrical properties have been measured by the one or more electrodes. In one or more exemplary methods, obtaining the monitor data comprises obtaining (e.g. receiving from one or more devices in the ostomy system, and/or retrieving from one or more devices in the ostomy system) localized monitor data with respect to a location and/or zone at the proximal side of the first adhesive layer of the base plate. In one or more exemplary methods, the localized monitor data may be with respect to a first location, a second location, a third location. In one or more exemplary methods, the localized monitor data may be with respect to a first zone, a second zone, and/or a third zone on proximal side of first adhesive layer of the base plate. The operating state of the ostomy appliance may be based on the moisture pattern type determined using e.g. parameter data obtained from one or more devices, such as a monitor device coupled with the base plate/electrode assembly having e.g. electrodes placed in respective zones of the base plate (such as electrodes of FIG. 6 and/or sensor points openings of FIG. 7).

In one or more exemplary methods, the monitor data may comprise first localized monitor data indicative of presence of fluid at a first location of the proximal side of the first adhesive layer of base plate or at a first zone of the proximal side of the first adhesive layer of base plate, second localized monitor data indicative of presence of fluid at a second location of the proximal side of the first adhesive layer of base plate or at a second zone of the proximal side of the first adhesive layer of base plate. For example, parameter data may comprise first parameter data indicative of the presence of fluid at a first zone and/or a primary sensing zone. For example, parameter data may comprise second parameter data indicative of the presence of fluid at a second zone and/or a secondary sensing zone. For example, parameter data may comprise third parameter data indicative of the presence of fluid at a third zone, and/or a tertiary sensing zone.

In one or more exemplary methods, determining the operating state of the ostomy appliance/ostomy system based on the monitor data comprises determining one or more moisture pattern types based on the monitor data, such as based on the ostomy data and/or the parameter data (e.g. first parameter data and optionally second parameter data), such as based on measurements obtained by the electrodes, such as measurements of resistance, capacitance and/or inductance, such as timing information, for e.g. a first primary sensing zone (and/or first zone), and optionally a second primary sensing zone (and/or second zone). The moisture pattern type is optionally indicative of leakage risk of the ostomy appliance and/or indicative of the risk of skin damage to the user of the ostomy system. In one or more exemplary methods, determining the operating state of the ostomy appliance based on the monitor data comprises determining one or more moisture pattern types based on the first parameter data (and optionally second parameter data and optionally a third parameter).

In one or more exemplary methods, determining one or more moisture pattern types may comprise selecting a moisture pattern type from a set of predefined moisture pattern types. The set of predefined moisture pattern types may comprise a number K of moisture pattern types, such as at least three moisture pattern types, at least four moisture pattern types, at least five moisture pattern types. The number K of moisture pattern types may be in the range from four to twenty.

In one or more exemplary methods, the method comprises determining whether the operating state satisfies a first primary criterion, and in accordance with a determination that the first primary criterion is satisfied, setting the operating state to the first primary operating state. The first primary criterion may comprise one or more criteria, such as first criteria, second criteria, third criteria. In one or more exemplary methods, the first primary criterion may be satisfied if the resistance between electrodes of an electrode pair, such as an outer or outermost electrode pair, of the electrode assembly is below a threshold.

In one or more exemplary methods, determining the operating state of the ostomy appliance based on the monitor data comprises determining the operating state based on the one or more moisture pattern types, such as determining that the operating state is the first primary operating state in accordance with the moisture pattern type being a first primary moisture pattern type. Several different moisture pattern types may be mapped to the same operating state. In other words, determining the operating state of the ostomy appliance/ostomy system/base plate, may comprise determining a moisture pattern type based on the monitor data and mapping the moisture pattern type to an operating state.

International patent application no. PCT/DK2018/050396 assigned to the applicant discloses examples of determining an operating state of an ostomy appliance/ostomy system.

In one or more exemplary methods, the interface comprises one or more of an audio interface, a visual interface, such as a display, and a transceiver module.

In one or more exemplary methods, communicating an indication via the display comprises displaying, on a visual interface (e.g. a display) of the accessory device, a user interface comprising one or more user interface objects representative of the indication, such as first primary user interface object(s) representative of a first primary operating state in a first time period, and a second user interface object(s) representative of the first primary operating state in a second time period. A user interface object may be representative of one or more moisture pattern types determined, such as a first moisture pattern type, a second moisture pattern type, and/or a third moisture pattern type.

A user interface object may comprise one or more visual indicators representative of the operating state in the respective time period, such as a first visual indicator, a second visual indicator, and/or third visual indicator. A visual indicator may be a text prompt indicating to the user the operating state of the ostomy appliance and or a possible reason for the operating.

In one or more exemplary methods/accessory devices, communicating an indication comprises notifying the user via the interface, such as by displaying a notification on a display of the accessory device, such as on a lock screen and/or a home screen. The notification may comprise the user interface object representative of or associated with the operating state in the respective time period. The notification may comprise a notification indicator to open an application related to the ostomy appliance. The method may comprise detecting an input on the notification indicator, in response to the input, opening the application related to the ostomy appliance, and in response to the opening of the application, displaying, on a display of the accessory device, the user interface object representative of or associated with the operating state in the respective time period.

The memory may be configured to store the monitor data and/or the operating state. The interface is configured to communicate indications to the user via the interface, such as an audio interface, a visual interface, and/or a transceiver module. An audio interface comprises for example a loudspeaker and/or a microphone. A visual interface comprises for a display, such as a touch sensitive touch-screen. A transceiver module comprises for example an antenna and/or a radio transceiver.

The processor may be configured to instruct the interface to display a user interface including user interface object(s).

The accessory device may comprise a user application configured to communicate the indications via the interface. The user application may be a dedicated ostomy application that assist the user in monitoring the internal leakage state of the ostomy appliance/ostomy system, and thereby reduce the likelihood of severe leakage reaching out to clothing of the user.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile device). The monitor device 6 is connectable or connected to electrode assembly/the base plate 4 via respective first connectors of the monitor device 6 and base plate 4. The monitor device 6 is configured for wireless communication with the accessory device 8, i.e. the monitor device is wirelessly connected or wirelessly connectable to the accessory device. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8, and the accessory device 8 is configured to obtain, such as receive, monitor data from the monitor device. The base plate 4 comprises a coupling member 14 in the form of a coupling ring 16 for coupling an ostomy pouch (not shown) to the base plate (two-part ostomy appliance). The base plate has a stoma-receiving opening 18 with a stoma centre point. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
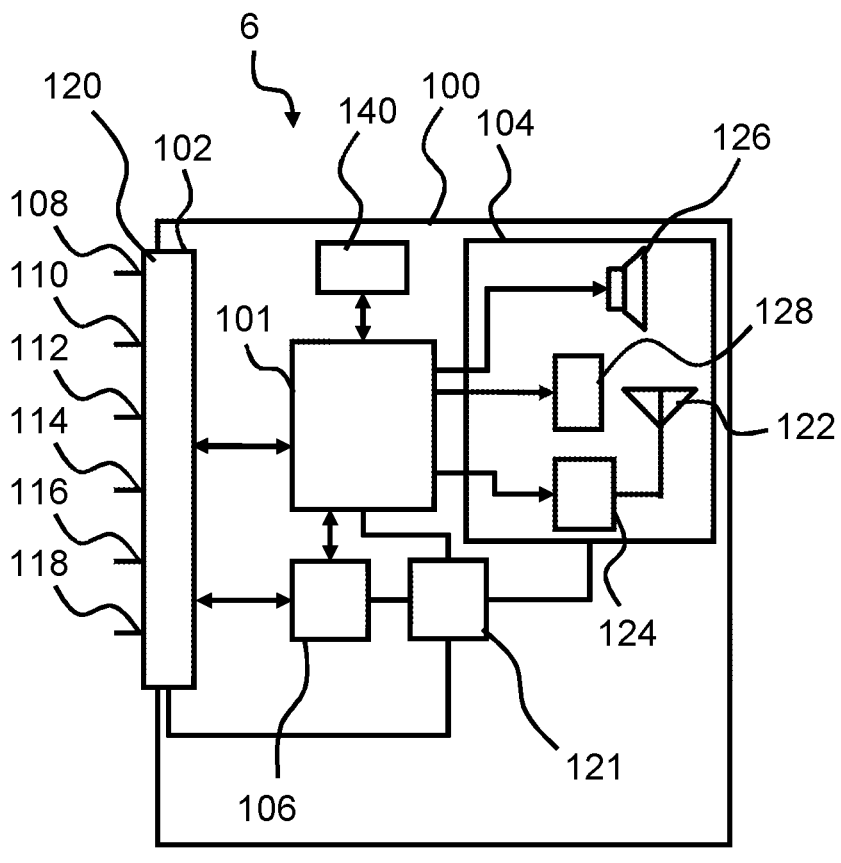
FIG. 2 illustrates an exemplary monitor device of the ostomy system.

FIG. 2 is a schematic block diagram of an exemplary monitor device. The monitor device 6 comprises a monitor device housing 100, 101 and one or more interfaces, the one or more interfaces including a first interface 102 (appliance interface) and a second interface 104 (accessory interface).

The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The monitor device 6/processor 101 is configured to obtain appliance data, such as ostomy data or parameter data based on ostomy data, based on appliance measurements via the terminals 108, 110, 112, 114, 116, and 118 of the first interface 102. The processor is configured to determine monitor data based on the appliance data. The monitor device 6/processor 101 is configured to wirelessly transmit the monitor data to the accessory device 8 via the second interface 104.

Figure 3:
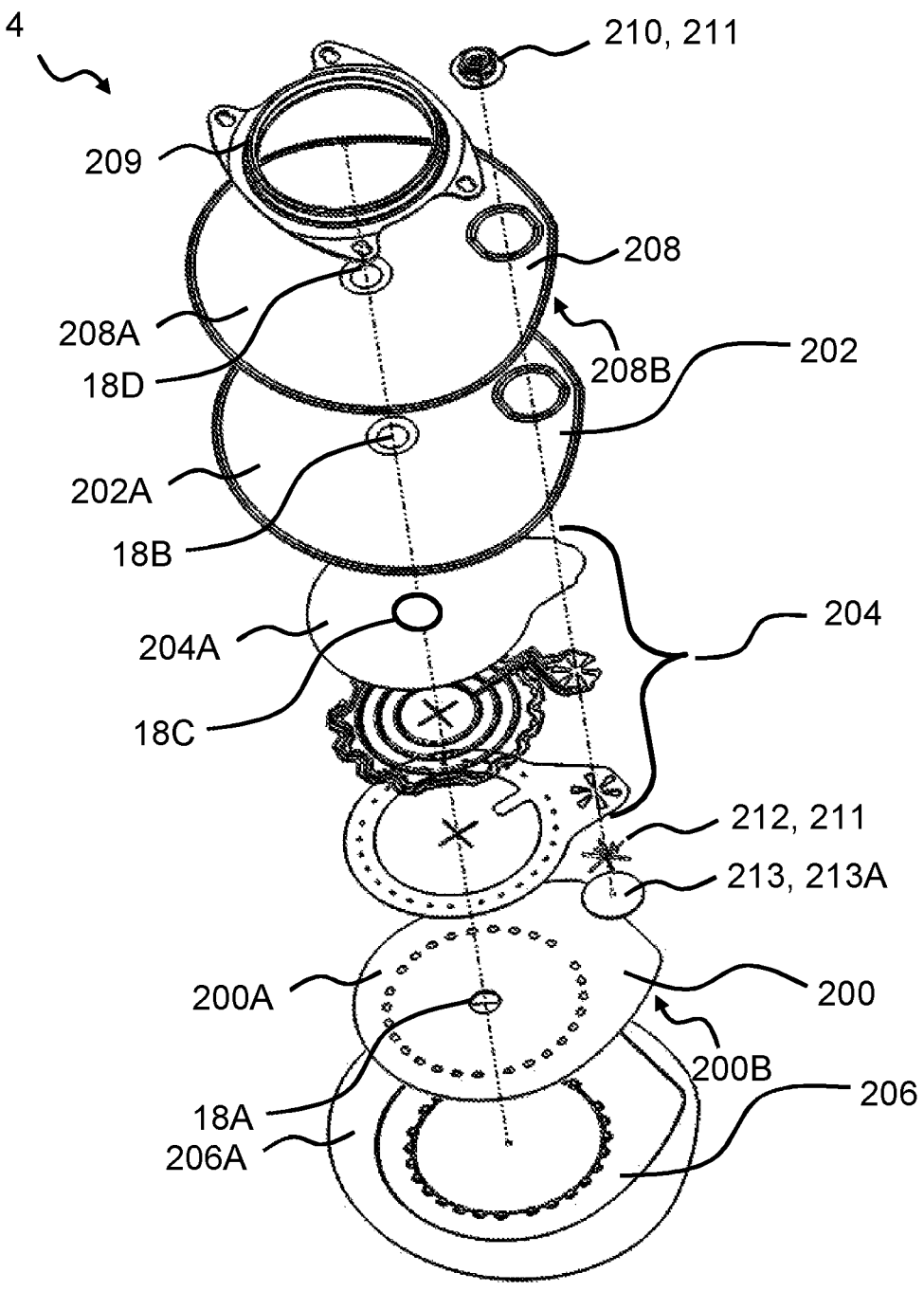
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin.

The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
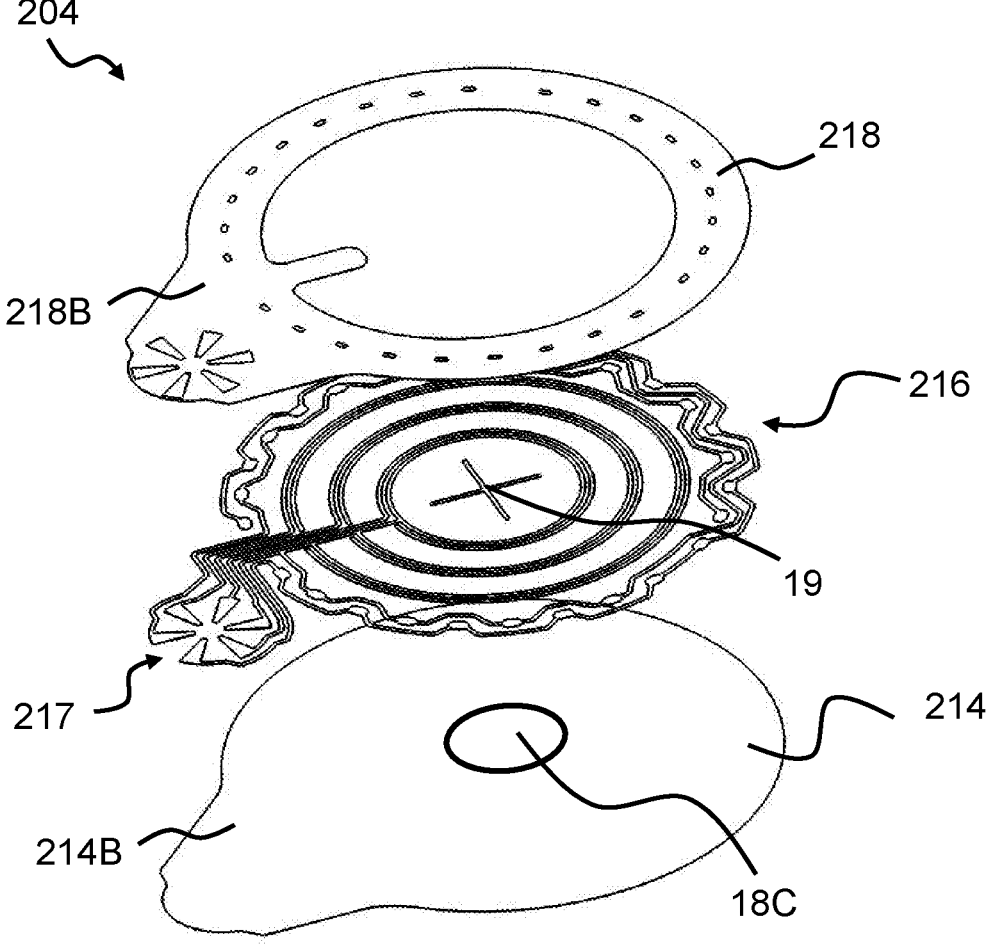
FIG. 4 is an exploded view of an exemplary electrode assembly.

FIG. 4 illustrates an exploded view of an exemplary electrode assembly 204 of a base plate. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figures 5, 6:
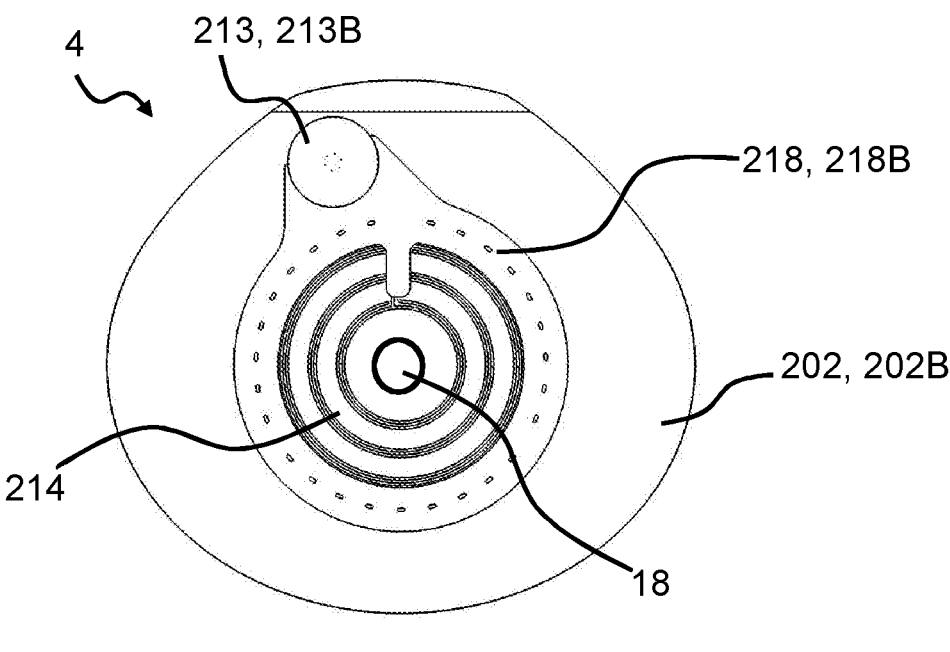
FIG. 5 is a proximal view of parts of a base plate.
FIG. 6 is a distal view of an exemplary electrode configuration.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B

Figure 7:
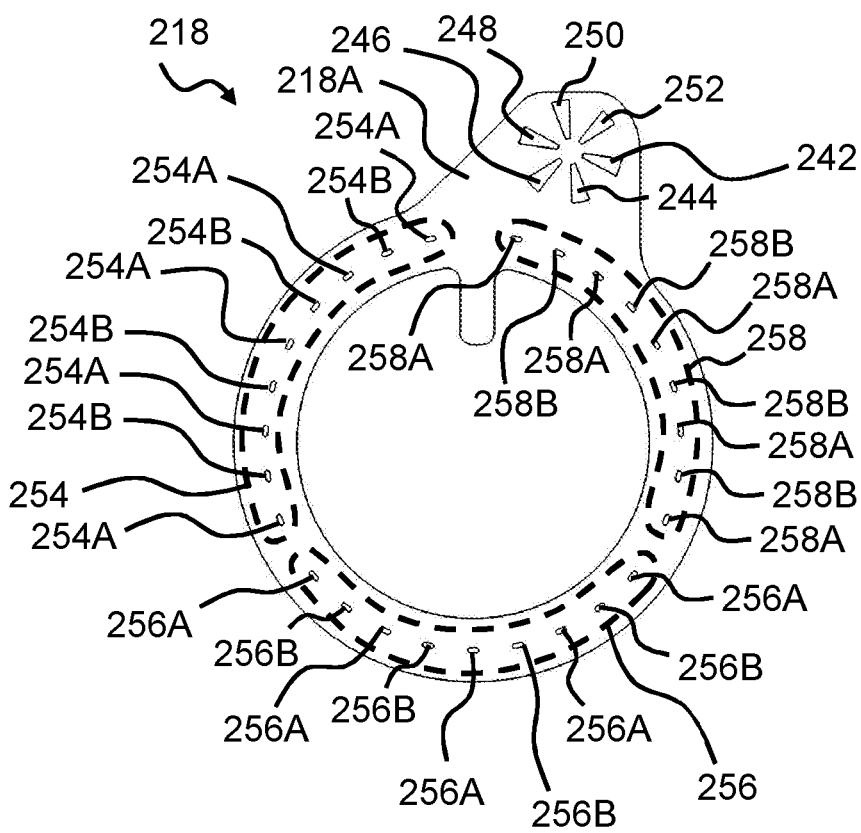
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
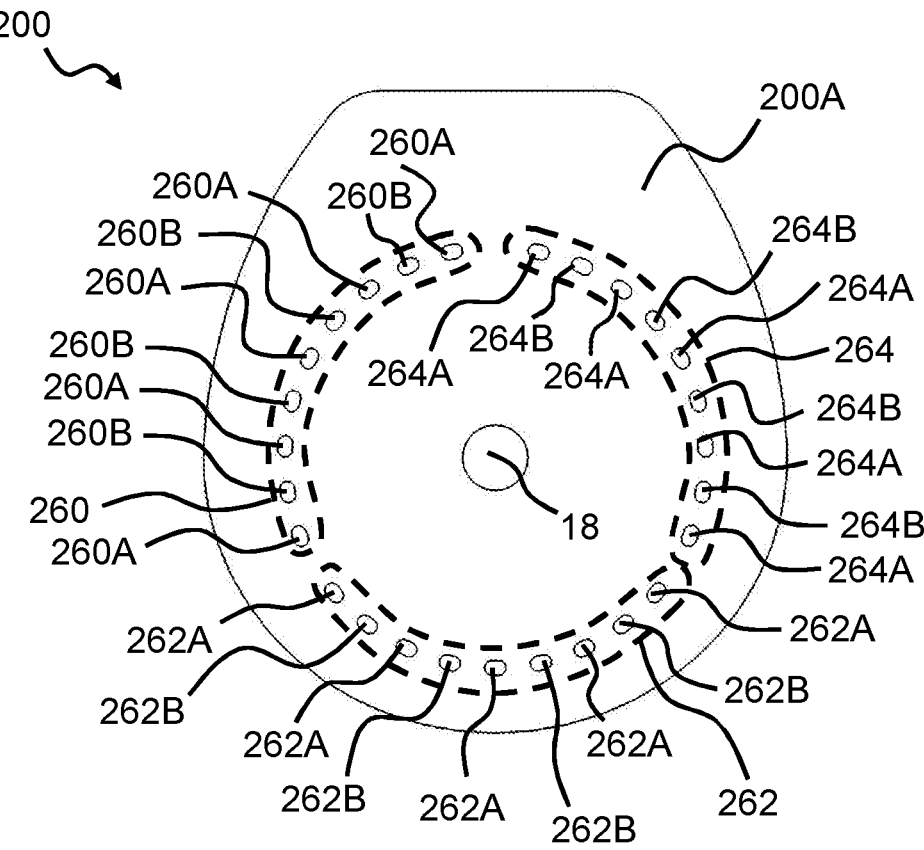
FIG. 8 is a distal view of an exemplary first adhesive layer.
Figure 9:
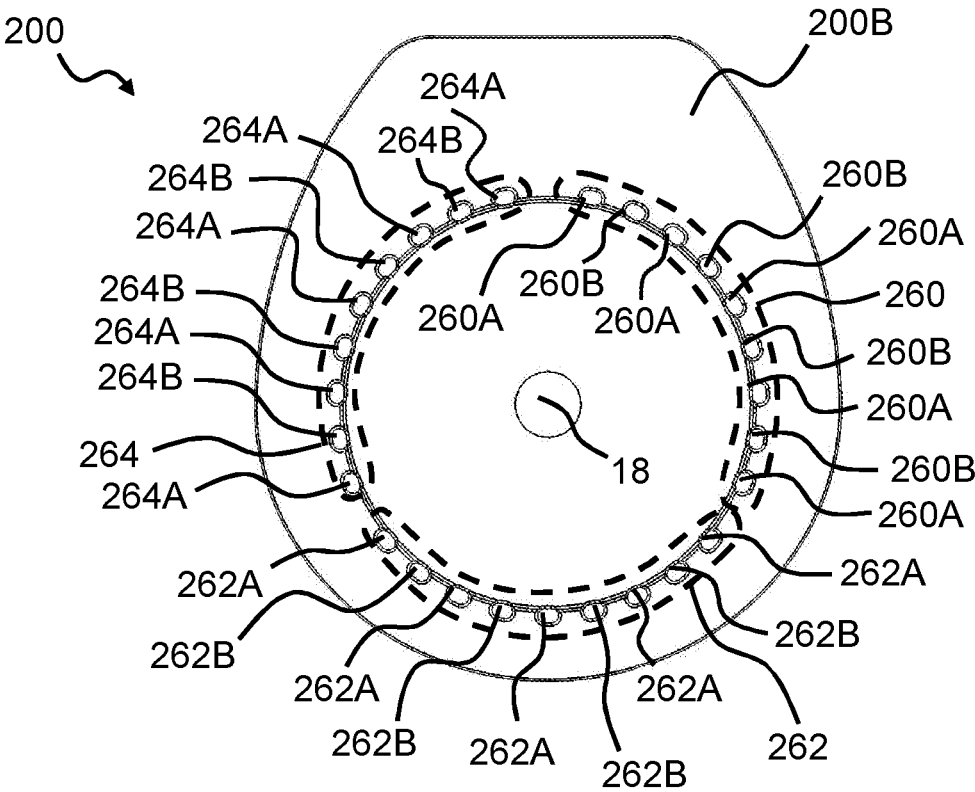
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
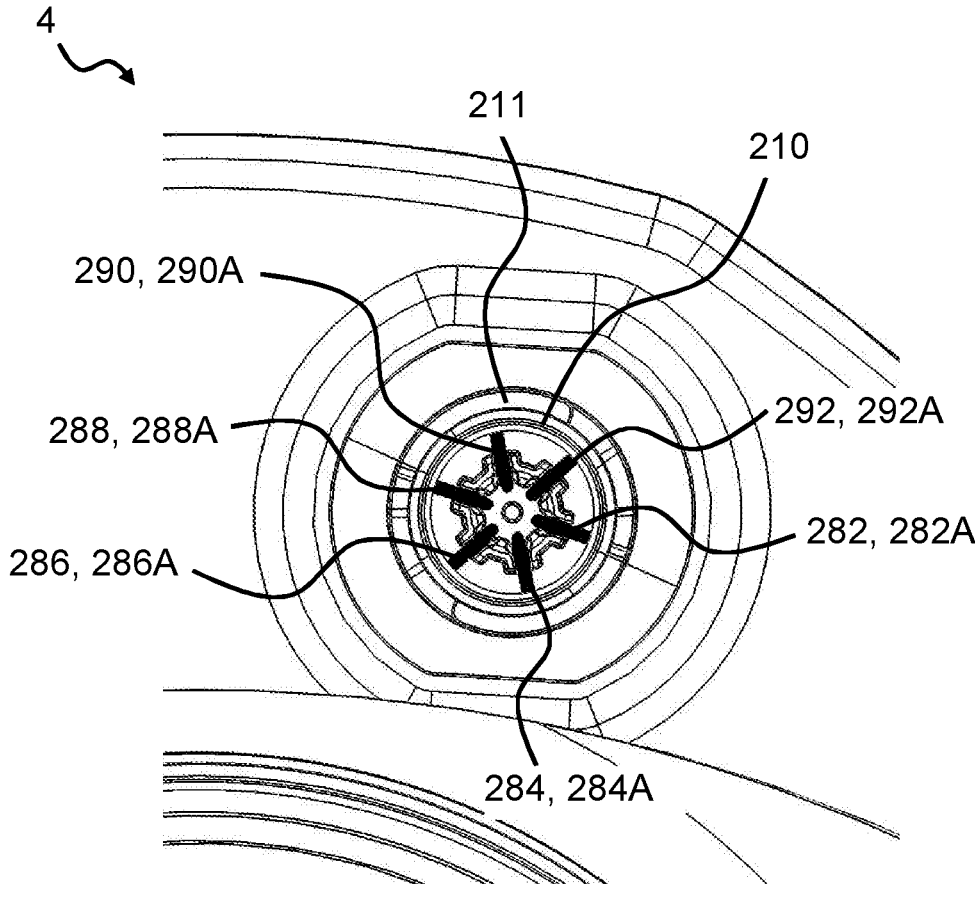
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 221/monitor interface comprises a plurality of terminals formed by respective terminal elements for forming respective electrical connections with respective terminals of the monitor device.

The plurality of terminals of the first connector 211/ monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
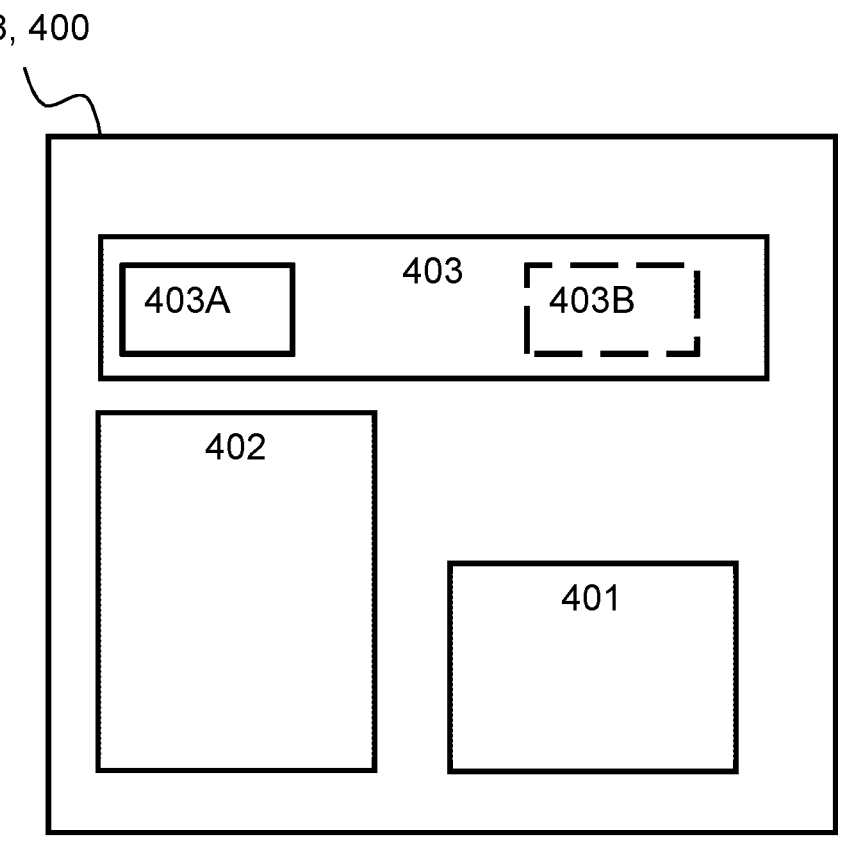
FIG. 11 illustrates an exemplary accessory device according to the present disclosure.

FIG. 11 is a block diagram illustrating an exemplary accessory device 400 according to the present disclosure. The accessory device 400 forms part of an ostomy system and is capable of supporting the monitoring of the operating state of an ostomy system/ostomy appliance/base plate to be placed on a user's skin. The accessory device 400 comprises a memory 401; a processor 402 coupled to the memory 401; and an interface 403, coupled to the processor 402.

Peripheral devices, such as memory 401 and/or interface 403 can be operatively and communicably coupled to the processor 402 via a bus for communicating data. The processor 402 can be a central processing unit (CPU), but other suitable microprocessors are also contemplated.

The interface 403 is configured to connect the accessory device to the monitor device of the ostomy system, the interface comprising a transceiver module 403A connected to the processor 402.

The interface 403 may be configured to communicate with one or more devices of the ostomy system. The one or more devices comprises a monitor device and/or an ostomy appliance configured to be placed on a skin surface of a user and/or on any additional seals. The interface 403 may comprise a display 403B as a visual interface to the user. The interface 403 is configured to establish a wireless connection between the monitor device and the accessory device.

The interface 403 is configured to receive monitor data from the monitor device, such as to receive or retrieve the monitor data. The monitor data may be indicative of a condition of one or more of the ostomy appliance, the monitor device, and the connection between the ostomy appliance and the monitor device, such as a condition of a proximal side of a first adhesive layer of the ostomy appliance that is directed towards the skin surface. In one or more exemplary accessory devices, the monitor data comprises appliance data, e.g. ostomy data, obtained via the interface 403 from an ostomy appliance.

The processor 402 may be configured to determine an operating state of the ostomy appliance based on the monitor data.

The processor 402 is configured to determine, based on the monitor data, an operating state of the ostomy system in a first time period, e.g. after a first event; in accordance with the operating state of the first time period being a first primary operating state, communicate a first primary indication via the interface; determine, based on the monitor data, an operating state of the ostomy system in a second time period, e.g. after the first time period or after a second event; and in accordance with the operating state of the second time period being the first primary operating state, communicate a second indication different from the first primary indication via the interface.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output, such as user interface objects displayed on the display, optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. The first user interface may be associated with the first time period and/or the second user interface may be associated with the second time period. A user interface may comprise one or more, such as a plurality of user interface objects. For example, the first user interface may comprise a first primary user interface object and/or a first secondary user interface object. A second user interface may comprise a second user interface object or a plurality of second user interface objects, such as second primary user interface object and/or a second secondary user interface object. A user interface object, such as the first primary user interface object and/or the second user interface object, may represent/be indicative of an operating state of the base plate in a time period.

The accessory device 400 is optionally configured to receive, via the interface 403, a user input indicative of the first event.

The ostomy appliance optionally comprises an ostomy pouch and a base plate, the base plate comprising a first adhesive layer having a proximal side, and one or more electrodes configured to measure electrical properties at or in the first adhesive layer, and in accessory device 400, to obtain the monitor data may comprise to obtain ostomy data representative of the electrical properties.

In accessory device 400, the first time period has a first period length less than 15 minutes. The first period length may be less than 10 minutes, such as in the range from 1 second to 5 minutes, such as 2 minutes, 3 minutes or 4 minutes. In one or more exemplary methods, the first time period has a first period length less than 1 minute, such as in the range from 15 seconds to 45 seconds. A relatively short first time period, such as less than 1 minute, may be sufficient to detect possible mishandling while not delaying the user in the application routine.

In accessory device 400, the first primary operating state may be indicative of presence of liquid or fluid, such as output, mucus, water, and/or sweat, on a proximal side of the base plate.

In one or more exemplary accessory devices, the interface 403 comprises a display 403B, and wherein to communicate the first primary indication comprises to display, on the display, a first primary user interface object. The first primary user interface object may be indicative of a wet mount of the ostomy appliance.

A user interface refers herein to a graphical representation comprising a collection of user interface objects. A user interface comprises one or more user interface objects. A user interface may be referred to as a user interface screen or a graphical user interface.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user, and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

In accessory device 400, to communicate the second primary indication optionally comprises to display, on a display of the accessory device, a second user interface object indicative of a possible leakage of output.

In accessory device 400, accessory device 400 is optionally configured to in accordance with the operating state in the first time period being a first secondary operating state, communicate a first secondary indication via the interface.

The first secondary operating state may be indicative of faulty connection between the ostomy appliance and the monitor device. In other words, the accessory may be configured to determine that the connection between the monitor device and the ostomy appliance/sensor assembly is faulty and in accordance with a determination that the connection is faulty, communicate a first secondary indication via the interface. The first secondary indication may represent the first secondary operating state.

Figure 12A:
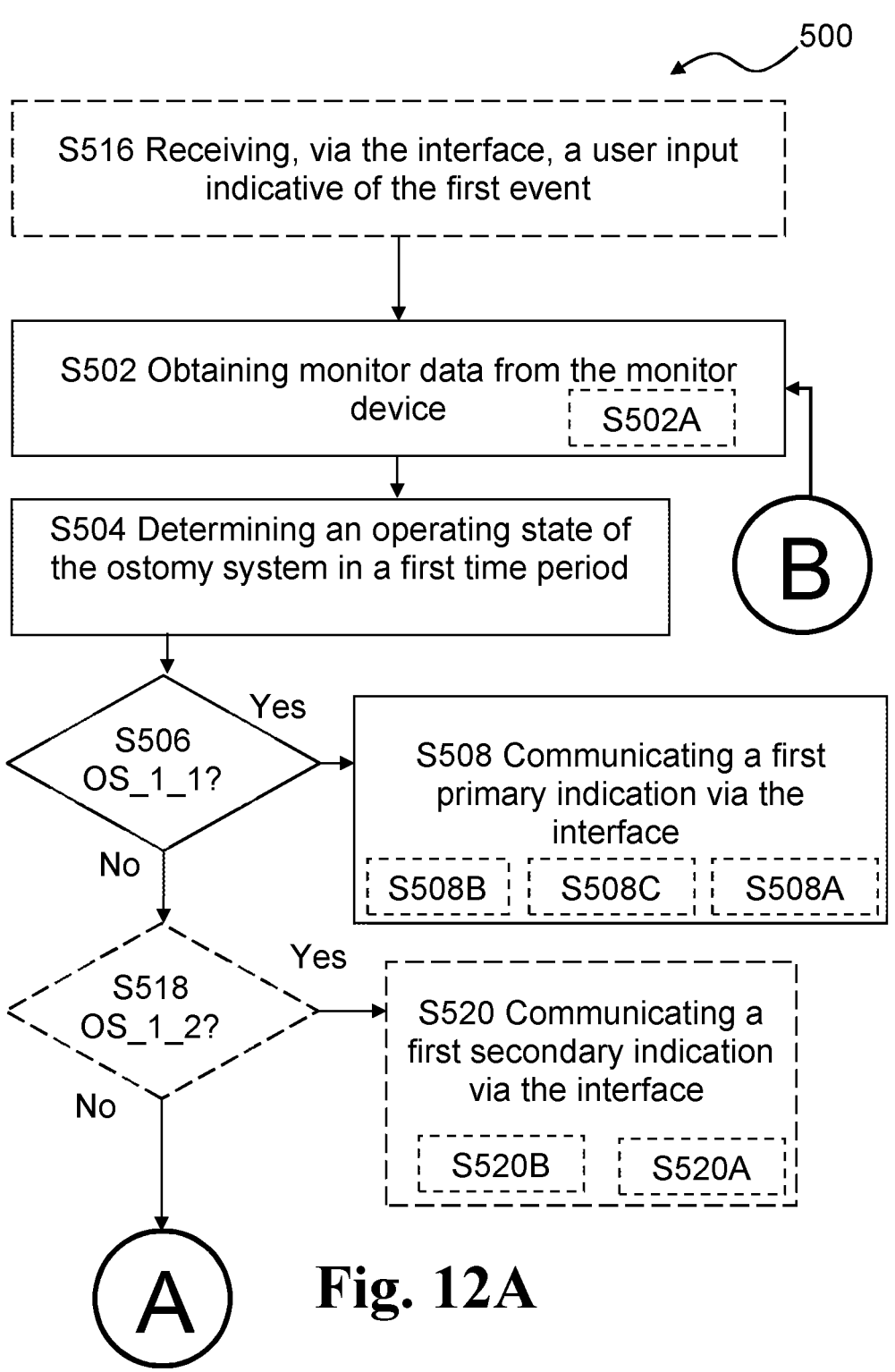
FIGS. 12A and 12B illustrate an exemplary method for monitoring an ostomy system.
Figure 12B:
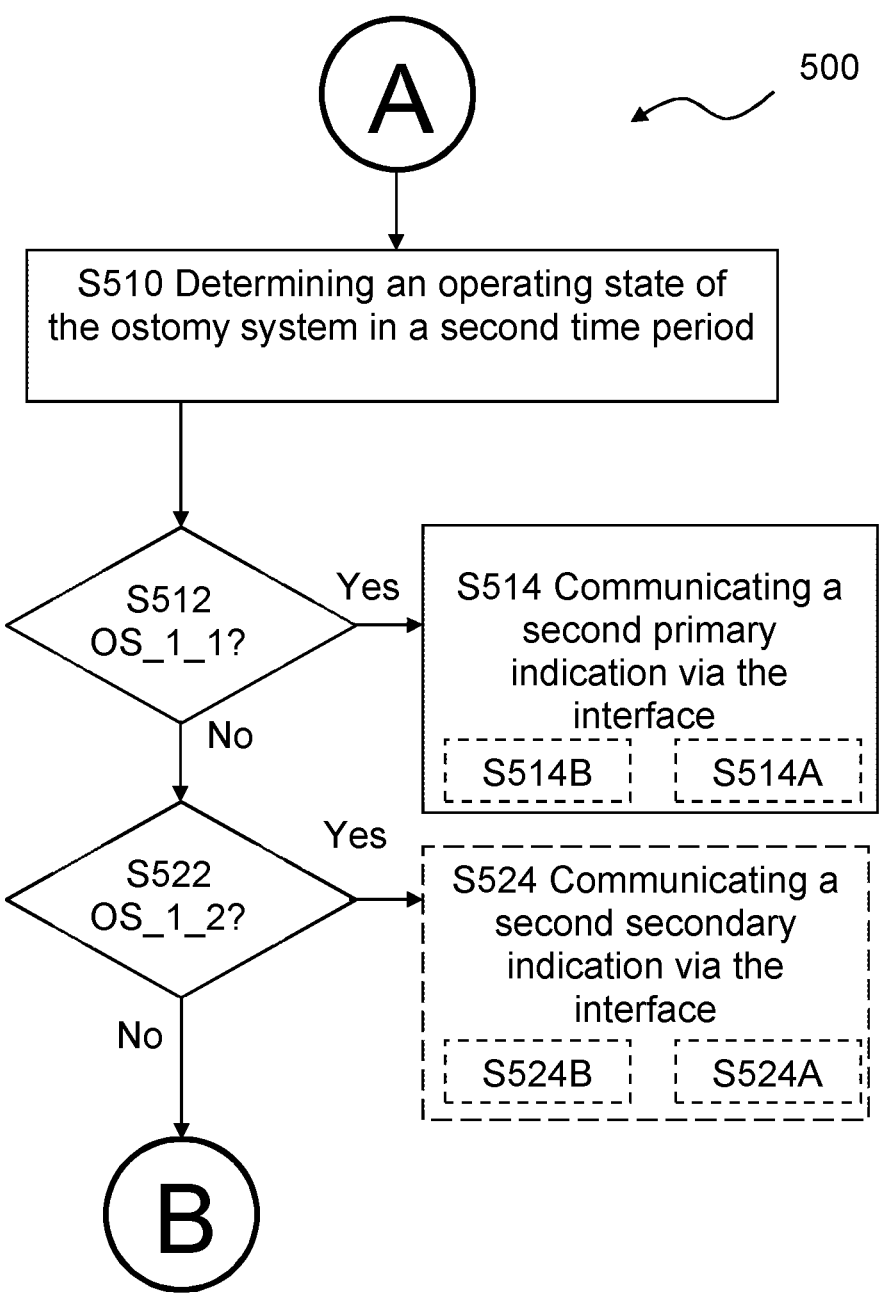

In accessory device 400, to communicate the first secondary indication optionally comprises to display, on the display, a first secondary user interface object indicative of a faulty connection between the monitor device and the ostomy appliance The processor 402 is optionally configured to perform any of the operations disclosed in FIGS. 12A and 12B.

The processor 402 may be optionally configured to perform any of the operations disclosed in FIGS. 12A and 12B (such as any one or more of S504, S506, A508, S508A, S508B, S510, S512, S514, S514A, S514B, S516, S518, S520, S520A, S520B, S522, S522A, S522B). The operations of the accessory device 400 may be embodied in the form of executable logic routines (such as, lines of code, software programs, etc.) that are stored on a non-transitory computer readable medium (such as, the memory 401) and are executed by the processor 402).

Furthermore, the operations of the accessory device 400 may be considered a method that the accessory device 400 is configured to carry out. Also, while the described functions and operations may be implemented in software, such functionality may as well be carried out via dedicated hardware or firmware, or some combination of hardware, firmware and/or software.

The memory 401 may be one or more of a buffer, a flash memory, a hard drive, a removable media, a volatile memory, a non-volatile memory, a random access memory (RAM), or other suitable device. In a typical arrangement, the memory 401 may include a non-volatile memory for long term data storage and a volatile memory that functions as system memory for the processor 402. The memory 401 may exchange data with the processor 402 over a data bus. Control lines and an address bus between the memory 401 and the processor 402 also may be present (not shown in FIG. 4). The memory 401 is considered a non-transitory computer readable medium.

FIGS. 12A and 12B shows a flow diagram of an example method 500 for monitoring an ostomy system. The ostomy system comprises a monitor device and an ostomy appliance comprising a base plate configured to be placed on a skin surface of a user. The method 500 is a method, performed in an accessory device, for monitoring an ostomy system comprising a monitor device and an ostomy appliance comprising a base plate configured to be placed on a skin surface of a user, the accessory device comprising an interface configured to communicate with at least the monitor device of the ostomy system. The method 500 comprises obtaining S502 monitor data from the monitor device, the monitor data being indicative of a condition of the ostomy system and determining S504, based on the monitor data, an operating state of the ostomy system, e.g. an operating state of the base plate, in a first time period e.g. after a first event.

The method 500 optionally comprises determining S506 whether the operating state of the first time period is a first primary operating state, and in accordance with the operating state of the first time period being a first primary operating state, OS_1_1, communicating S508 a first primary indication via the interface. Communicating S508 the first primary indication optionally comprises displaying S508A, on a display of the accessory device, a first primary user interface object. Communicating S508 the first primary indication optionally comprises outputting S508C a first primary audio output. Thereby, the chance of the user noting the first primary indication may be increased, which may be important shortly after application of the ostomy appliance. Further, the need for privacy in notifications may not be important in a first time period, since the user has just applied a new ostomy appliance and therefore in any case is in a private situation.

The first primary operating state is optionally indicative of presence of liquid or fluid, such as water, output, sweat, and/or mucus, on a proximal side of the base plate. The first primary user interface object may be indicative of a mishandling of the ostomy appliance, e.g. during application of the base plate, such as indicative of a wet mount of the ostomy appliance. A wet mount is understood as liquid, such as water, sweat, mucus, and/or output, being present between the first adhesive layer of the base plate/electrode assembly and the skin of the user during and/or shortly after (i.e., within the first time period) application of the base-plate.

The method 500 comprises determining S510, based on the monitor data, an operating state of the ostomy system in a second time period, e.g. after the first time period and/or after a second event; optionally determining S512 whether the operating state of the second time period is the first primary operating state; and in accordance with the operating state of the second time period being the first primary operating state, communicating S514 a second primary indication different from the first primary indication via the interface. Communicating S514 the second primary indication optionally comprises displaying S514A, on a display of the accessory device, a second primary user interface object.

In method 500, the operating state of the ostomy system may comprise an operating state of the base plate, the operating state of the base plate optionally being indicative of an adhesive performance of the base plate and/or indicative of presence of fluid, such as one or more of output, water, sweat, and mucus, on the proximal side or surface of the first adhesive layer. In method 500, the operating state of the ostomy system may comprise an operating state of the ostomy appliance and/or an operating state of a connection between the ostomy appliance and the monitor device.

The first event may be a connection event of the monitor device being connected to the ostomy appliance. A connection event of the monitor device being connected to the ostomy appliance may be detected by the monitor and a connection indicator, such as a connection time stamp, may be included in the monitor device. The first event may be an application event of the ostomy appliance being applied on the skin of the user. The first event may be a connection event of the monitor device being connected to the accessory device. A connection event of the monitor device being connected to the accessory device may be detected by the accessory device. The first event may be a user input event of a user input indicative of the first event, i.e. where the accessory device detects a user input, e.g. on a user interface object on touch sensitive display.

In method 500, an end of the first period may trigger or be the beginning of the second period. In other words, the first period and the second period may be separate and non-overlapping. In one or more exemplary methods, a second event may trigger or be the beginning of the second period. The second event may be a user input event of a user input indicative of the second event, i.e. where the accessory device detects a user input, e.g. on a user interface object on touch sensitive display. The second event may be a time after a user input event of a user input indicative of the second event, such as 30 seconds after the user has indicated that the ostomy system is ready for use, i.e. that the application routine is done. The monitor data may be indicative of a physical condition of a base plate, e.g. indicative of a dynamic internal state of the base plate. The monitor data may be indicative of moisture presence in the base plate/first adhesive layer and/or at the first adhesive layer, such as between the first adhesive layer and the skin of a user.

The method 500 optionally comprises receiving S516, via the interface, a user input indicative of the first event, e.g. via touch-sensitive display, such as by a user tapping a user interface object of a user interface.

In method 500, the ostomy appliance comprises a base plate, the base plate comprising a first adhesive layer having a proximal side, and one or more electrodes configured to measure electrical properties at or in the first adhesive layer, wherein obtaining the monitor data optionally comprises obtaining ostomy data S502A representative of the measurement of the electrical properties.

In one or more exemplary methods for monitoring an ostomy system, the first time period has a first period length less than 15 minutes. The first period length may be less than 10 minutes, such as in the range from 1 second to 5 minutes, such as 2 minutes, 3 minutes or 4 minutes. In one or more exemplary methods, the first time period has a first period length less than 1 minute, such as in the range from 15 seconds to 45 seconds. A relatively short first time period, such as less than 1 minute, may be sufficient to detect possible mishandling while not delaying the user in the application routine.

The method may comprise determining S508B a first primary indication e.g. based on a first time after the first event or start of the first time period. The first primary user object may indicate one or more of the first time, the first primary operating state, a reason for the first primary operating state, and a recommended action. The first primary user object may comprise first primary text. Examples of first primary text may be "Liquid has been detected between the base plate and your skin. This may be due to a misapplication of your baseplate", "Your skin is wet. Please change your base plate and make sure to dry or clean your skin properly". "Liquid was detected 10 seconds after application due to a wet mount of your base plate. Please change". Determining S508B a first primary indication may comprise selecting a first primary user interface object from a set of user interface objects.

In method 500, communicating S514 the second primary indication optionally comprises displaying S514A, on a display of the accessory device, a second primary user interface object, e.g. indicative of a possible leakage of output.

The method may comprise determining S514B a second primary indication e.g. based on a second time after the second event or start of the second time period. The second primary user object may indicate one or more of the second time, the first primary operating state, a reason for the first primary operating state, and a recommended action. The second primary user object may comprise second primary text. Examples of second primary text may be "Liquid has been detected between the base plate and your skin. There is a high risk of leakage", "Check your base plate. A leakage could be imminent".

The second primary user object may be split into a plurality of second primary user interface objects. Determining a second primary indication may comprise selecting as second primary user interface object from a set of user interface objects.

The method 500 optionally comprises determining S518 whether the operating state of the first period is a first secondary operating state, and, in accordance with the operating state in the first time period being a first secondary operating state OS_1_2, communicating S520 a first secondary indication via the interface. The first secondary operating state may be indicative of a mishandling of the monitor device during coupling of the ostomy appliance/ electrode assembly and/or be indicative of faulty connection between the ostomy appliance and the monitor device. In method 500, communicating S520 the first secondary indication optionally comprises displaying S520A, on a display of the accessory device, a first secondary user interface object. The first secondary user interface object may be indicative of a faulty connection between the monitor device and the ostomy appliance, e.g. due to presence of liquid in the connection between the monitor device and the ostomy appliance, such as comprising a first secondary text, e.g. "The connection between monitor device and ostomy appliance is wet. Please keep the connection dry".

The method 500 optionally comprises determining S522 whether the operating state of the second time period is the first secondary operating state OS_1_2. The method 500 optionally comprises, in accordance with the operating state in the second time period being a first secondary operating state, communicating S524 a second secondary indication via the interface. The second secondary indication may be different from the first secondary indication. Communicating S524 a second secondary indication via the interface may comprise displaying S524A a second secondary user interface object, e.g. different from the first secondary user interface object. The second secondary user interface object may be indicative of water ingress in the connection between the monitor device and the ostomy appliance in the second time period. For example, the second secondary user interface object may comprise a second secondary text, e.g. "Water ingress has occurred in the connection after application. Please clean and dry the connection".

Figure 13:
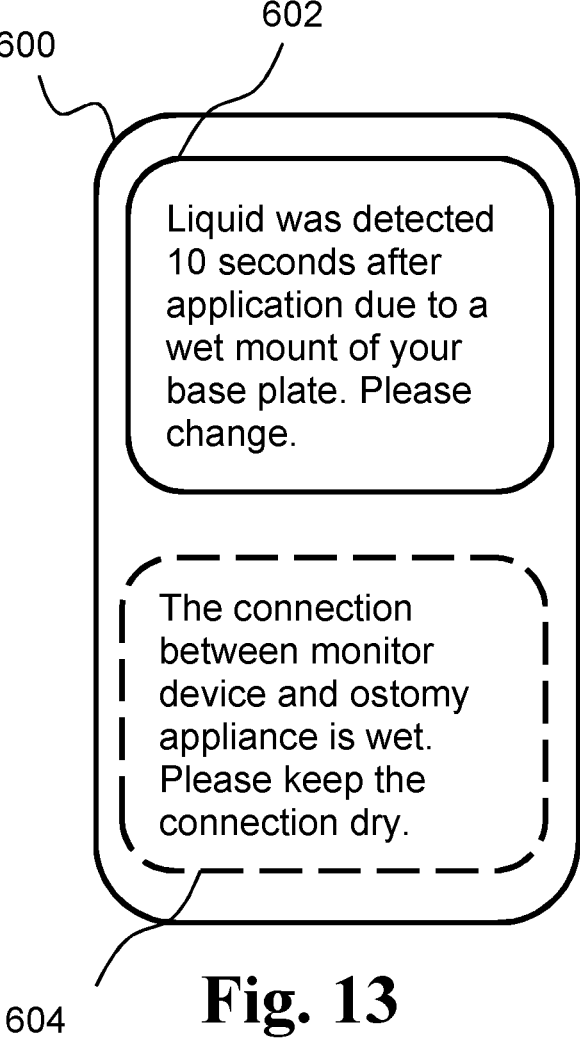
FIG. 13 illustrates a first user interface.

FIG. 13 illustrates an exemplary user interface for communicating an operating state of an ostomy system via an accessory device, such as via a visual interface or display of the accessory device in a first time period.

The first user interface 600 is optionally displayed during the first time period after the first event. The first user interface 600 comprises a first primary user interface object 602 displayed in accordance with a determination that the operating state in the first time period is a first primary operating state. The first primary user interface object 602 optionally comprises a first primary text such as "Liquid was detected 10 seconds after application due to a wet mount of your base plate. Please change", e.g. based on and/or including a first time (10 seconds) of determining the operating state, the reason (wet mount) for the operating state and a recommended action (please change).

The first user interface 600 optionally comprises a first secondary user interface object 604 displayed in accordance with a determination that the operating state in the first time period is a first secondary operating state. The first secondary user interface object 604 optionally comprises a first secondary text such as "The connection between monitor device and ostomy appliance is wet. Please keep the connection dry."

The accessory device is configured to change dynamically the visual appearance of the first user interface 600 in accordance with the operating state of the ostomy system, such as the operating state of the base plate.

Figure 14:
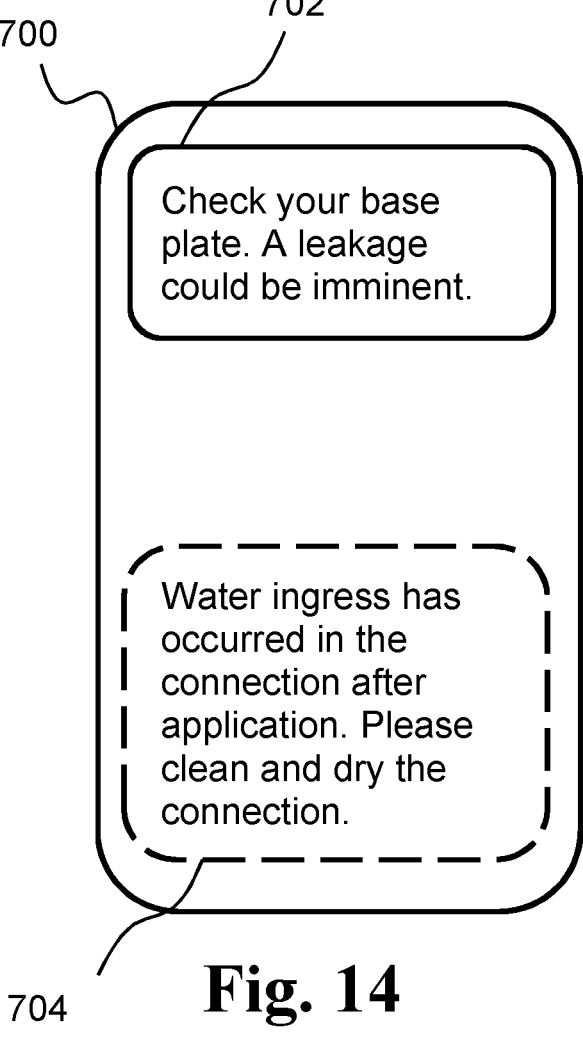
FIG. 14 illustrates second user interface.

FIG. 14 illustrates an exemplary user interface for communicating an operating state of an ostomy system via an accessory device, such as via a visual interface or display of the accessory device in a second time period.

The second user interface 700 is optionally displayed during the first time period after the first event. The second user interface 700 comprises a second primary user interface object 702 displayed in accordance with a determination that the operating state in the second time period is a first primary operating state. The second primary user interface object 702 is different from the first primary user interface object and optionally comprises a second first primary text such as "Check your base plate. A leakage could be imminent".

The second user interface 700 optionally comprises a second secondary user interface object 704 displayed in accordance with a determination that the operating state in the second time period is a first secondary operating state, e.g. where fluid is detected in the connection between the monitor device and the ostomy appliance. The second secondary user interface object 704 optionally comprises a second secondary text such as "Water ingress has occurred in the connection after application. Please clean and dry the connection".

The accessory device is configured to change dynamically the visual appearance of the second user interface 700 in accordance with the operating state of the ostomy system, such as the operating state of the base plate.

The monitor data may be seen as indicative of the operating state of the ostomy system/appliance. The visual appearance of the visual indicators is indicative of the operating state of the ostomy appliance, such as indicative of the moisture pattern type determined by the accessory device.

The accessory device may be configured to provide the user interfaces 600 and 700 of FIGS. 13 and 14 in a user application running on the processor. The accessory device may comprise a user application configured to communicate the indications via the interface. The user application may be a dedicated ostomy application that assist the user in monitoring the internal operating state of the ostomy appliance, and thereby reduce the likelihood of severe leakage reaching out to clothing of the user.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-14 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stoma-receiving opening
19 opening centre
20 docking station
22 first connector
24 docking station user interface
100 monitor device housing
101 processor
102 first interface 104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
218 masking element
218A distal surface of masking element
218B proximal surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening 248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
400 accessory device
401 accessory device memory
402 accessory device processor
403 accessory device interface
500 method, performed in an accessory device, for monitoring an ostomy system
S502 obtaining monitor data from the monitor device
S502A obtaining ostomy data representative of the measurement of the electrical properties
S504 determining, based on the monitor data, an operating state of the ostomy system
S506 determining whether the operating state of the first time period is a first primary operating state
S508 communicating a first primary indication via the interface
S508A displaying, on a display of the accessory device, a first primary user interface object
S508B determining a first primary indication
S508C outputting a first primary audio signal
S510 determining, based on the monitor data, an operating state of the ostomy system in a second time period
S512 determining S512 whether the operating state of the second time period is the first primary operating state
S514 communicating a second primary indication different from the first primary indication via the interface.
S514A displaying, on a display of the accessory device, a second primary user interface object
S514B determining a second primary indication
S516 receiving, via the interface, a user input indicative of the first event
S518 determining whether the operating state of the first period is a first secondary operating state S520 communicating a first secondary indication via the interface S520A displaying, on a display of the accessory device, a first secondary user interface object S520A determining a first secondary indication S522 determining whether the operating state of the second time period is the first secondary operating state S524 communicating a second secondary indication via the interface S524A displaying a second secondary user interface object S524 determining a second secondary indication

600 first user interface

602 first primary user interface object

604 first secondary user interface object

700 second user interface

702 second primary user interface object

704 second secondary user interface object

The invention claimed is:

1. A method, performed in an accessory device, for monitoring an ostomy system comprising a monitor device and an ostomy appliance comprising a base plate configured to be placed on a skin surface of a user, wherein the accessory device comprises an interface configured to communicate with at least the monitor device of the ostomy system, the method comprising:

obtaining a first instance of monitor data from the monitor device, the first instance of monitor data being indicative of a condition of the ostomy system;

determining, based on the first instance of monitor data, an operating state of the ostomy system in a first time period after a first event;

in accordance with determining the operating state in the first time period, communicating a first primary indication via the interface;

determining, based on a second instance of monitor data, the operating state of the ostomy system in a second time period after the first time period; and in accordance with determining the operating state in the second time period instead of the first time period, communicating a second indication different from the first primary indication via the interface.

2. The method according to claim 1, wherein the method comprises receiving, via the interface, a user input indicative of the first event.

3. The method according to claim 1, wherein the ostomy appliance comprises a base plate, the base plate comprising a first adhesive layer having a proximal side, and one or more electrodes configured to measure electrical properties at or in the first adhesive layer, wherein obtaining the monitor data comprises obtaining ostomy data representative of the measurement of the electrical properties.

4. The method according to claim 1, wherein the first time period has a first period length less than 15 minutes.

5. The method according to claim 1, wherein the operating state is indicative of presence of liquid on a proximal side of the base plate.

6. The method according to claim 1, wherein communicating the first primary indication comprises displaying, on a display of the accessory device, a first primary user interface object indicative of a wet mount of the ostomy appliance.

7. The method according to claim 1, wherein communicating the second indication comprises displaying, on a display of the accessory device, a second user interface object indicative of a possible leakage of output.

8. The method according to claim 1, wherein the operating state is a first primary operating state and the method further comprises:

identifying a first secondary operating state indicative of faulty connection between the ostomy appliance and the monitor device; and in accordance with identifying the first secondary operating state, communicating a first secondary indication via the interface.

9. The method according to claim 8, wherein communicating the first secondary indication comprises displaying, on a display of the accessory device, a first secondary user interface object indicative of a faulty connection between the monitor device and the ostomy appliance.

\* \* \* \* \*